United States Patent [19]
Maksudian et al.

[11] Patent Number: 5,911,829
[45] Date of Patent: Jun. 15, 1999

[54] APPARATUS FOR DISPENSING STRING MATERIAL

[75] Inventors: Steven G. Maksudian, Libertyville, Ill.; Patrick J. Ferguson, Portland, Oreg.; Francis K. Walton, Farmersburg, Ind.

[73] Assignees: Mallinckrodt Veterinary, Inc., Mundelein, Ill.; CP Medical, Portland, Oreg.

[21] Appl. No.: 08/516,179

[22] Filed: Aug. 17, 1995

[51] Int. Cl.$^6$ .................................................. B05C 3/12
[52] U.S. Cl. .................................... 118/420; 118/123
[58] Field of Search ................... 242/588.6, 588.3, 242/172, 599.3; 132/322, 323, 324; 206/63.3, 63.5, 409, 416; 118/420, 123, 423

[56] References Cited

U.S. PATENT DOCUMENTS

| | | | |
|---|---|---|---|
| 226,182 | 4/1880 | Merrell | 242/588.6 |
| 408,625 | 8/1889 | Johnson . | |
| 418,271 | 12/1889 | Buckmaster . | |
| 529,844 | 11/1894 | Stratton | 206/63.3 |
| 551,147 | 12/1895 | Stratton | 206/63.3 |
| 554,040 | 2/1896 | Stratton | 206/63.3 |
| 959,781 | 5/1910 | Moyer | 242/588.6 |
| 1,103,227 | 7/1914 | Stratton | 206/63.3 |
| 1,473,376 | 11/1923 | Langenzen . | |
| 1,569,577 | 1/1926 | Robinson . | |
| 1,871,235 | 8/1932 | Proctor et al. . | |
| 2,128,701 | 8/1938 | Gelinsky . | |
| 3,376,973 | 4/1968 | Granowitz et al. . | |
| 3,525,462 | 8/1970 | Freedman | 242/588.3 |
| 3,545,608 | 12/1970 | Berger et al. . | |
| 3,592,203 | 7/1971 | Johnson | 132/323 |
| 3,830,247 | 8/1974 | Kaphalakos | 132/322 |
| 3,902,510 | 9/1975 | Roth | 132/355 |
| 3,930,059 | 12/1975 | Wells . | |
| 4,109,522 | 8/1978 | Elbreder | 132/325 |
| 4,294,418 | 10/1981 | Gell . | |
| 4,582,196 | 4/1986 | Hughson et al. | 206/63.3 |
| 5,065,861 | 11/1991 | Greene et al. | 242/171 |
| 5,109,983 | 5/1992 | Malone et al. . | |

FOREIGN PATENT DOCUMENTS

| | | |
|---|---|---|
| 1139492 | 7/1957 | France . |
| 2324315 | 4/1977 | France . |
| 670937 | 1/1939 | Germany . |
| 380290 | 7/1964 | Switzerland . |
| 494036 | 7/1970 | Switzerland . |
| 2267079 | 11/1993 | United Kingdom . |

*Primary Examiner*—Brenda A. Lamb
*Attorney, Agent, or Firm*—Lerner, David, Littenberg, Krumholz & Mentlik, LLP

[57] ABSTRACT

An apparatus for dispensing string material such as suture from a rotating spool housed in a sealed housing which is filled with a liquid, for example an antiseptic fluid. The housing forms a hollow member into which the spool of suture is disposed so as to be freely rotatable. An end of the suture extends from the interior of the housing through a wiper member so as to be grasped by a user. The suture spool comprises an increased diameter core member which allows the entire length of suture stored thereon to be usable in an uncoiled manner when removed from the device. The center portion or core of the suture spool has a closed periphery so as to reduce the amount of antiseptic required to fill the interior of the housing and maintain the suture sterile. Also, the sidewalls of the housing are provided with projections that engage the sidewalls of the spool to permit a user to grasp and apply force against the housing while withdrawing the suture without slowing or stopping rotation of the spool.

14 Claims, 3 Drawing Sheets

APPARATUS FOR DISPENSING STRING MATERIAL

BACKGROUND OF THE INVENTION

1. Field of the Invention

The present invention relates generally to apparatus for dispensing string material, such as suture, and, more particularly, to apparatus in which the string material is wound on a spool disposed in liquid.

2. Description of Background Art

Prior art suture dispensing apparatus comprise a housing in which a spool having suture wound thereabout is rotatably disposed. The housing is hollow and typically includes a liquid, for example, an antiseptic such as alcohol, in which the spool of suture is disposed to maintain the suture moist and/or sterile. The cost of the alcohol increases the production cost of the apparatus and, accordingly, it has been desired to reduce the amount of alcohol used in the dispenser. Further, due to government regulations, shipping costs are increased if the amount of alcohol exceeds a certain limit. For example, the prior art dispenser housing usually has a square or rectangular outer shape or periphery, the bottom panel thereof is often recessed into the housing to form an arcuate base surface which closely matches the contour of the spool. This recessed bottom reduces the size of the interior of the housing (relative the outer walls thereof) and thus decreases the amount of alcohol required to fill same. However, although prior art apparatus have attempted to reduce costs by reducing the amount of alcohol used to fill the housing, a considerable volume of alcohol is still required to adequately coat the suture, and thus there remains room in the art for improvement.

Prior art suture-dispensing apparatus are subject to various problems in addition to requiring a considerable amount of alcohol to fill the housing. In particular, the spools about which the suture is wound typically have a relatively small diameter, for example 1 inch. When a major portion of the suture has been dispensed from the spool, the remaining suture, i.e. the terminal section of the length of suture wound on the spool, remains tightly curled or coiled upon removal from the spool and is unusable. Consequently, use of prior art apparatus results in wasted suture which is too tightly coiled or otherwise distorted to use in medical procedures. As such, there is a need in the art for an improved suture-dispensing apparatus which avoids such problems.

Another problem with prior art suture dispensing apparatus relates to the handling of the device during operation. A user will typically hold the device in one hand, squeezing the opposite sidewalls of the container between the thumb and fingers, while grasping the free end of the suture with the other hand to withdraw and cut a desired length of suture. The user's one hand applies force and pressure against the sidewalls of the housing which flex inward toward the spool of suture. As the spool of suture typically is free-floating within the housing, i.e. it does not have an axle (to save costs), deflecting the sidewalls of the housing contacts and interferes with rotation of the spool. Specifically, a conventional spool is reel-shaped with a core extending between enlarged outer circular walls which support the suture wound about the core. The outer circular walls are adjacent to, but spaced slightly from, the interior of the sidewalls of the outer housing. Thus, squeezing the sidewalls of the housing toward each other often causes the housing walls to contact the walls of the rotating spool, thereby slowing or stopping such rotation. The user may continue to attempt to pull the free end of the suture away from the apparatus which, due to the spool being held or impeded from rotating, results in breaking the suture. These problems result in wasted suture and inefficient performance of medical procedures as well as overall frustration with the performance of the dispensing apparatus. Accordingly, there is a need in the art for an improved suture-dispensing apparatus free of such problems.

SUMMARY OF THE INVENTION

The present invention provides a suture-dispensing apparatus in which a spool of suture is disposed within the hollow interior of a housing member. The spool is free to rotate to dispense suture through an opening formed in the housing. The housing is filled, partially or completely, with a liquid, for example an antiseptic such as alcohol, to coat the suture and keep it moist and/or sterile. The spool includes a core having an outer surface about which the suture is wound. The core has an increased external size or diameter to prevent the terminal portion of the suture (i.e., nearest the core surface) from being tightly coiled upon removal from the spool. Also, the core of the spool is formed with a closed exterior which reduces the amount of liquid required to fill the housing. The spool may have a solid tubular core or a hollow tubular core. If the core is hollow, the open ends thereof are closed by cap members which may be enlarged to form the sides of the spool. Finally, the invention includes projections or nibs formed on, or attached to, the exterior of the sidewalls of the spool for contacting the interior of the sidewalls of the housing upon the application of force to the housing. The projections permit a user to squeeze the housing sidewalls with one hand and withdraw the suture with the other hand without such squeezing preventing or adversely affecting spool rotation and withdrawal of the suture. Alternatively, one or more of the projections may be formed on the interior of the housing walls to contact the spool. In a further embodiment, the spool core has an axle therein and the ends of the axle project outward to contact the housing walls and prevent braking of the rotating spool.

DETAILED DESCRIPTION OF PREFERRED EMBODIMENTS

Figure 1:
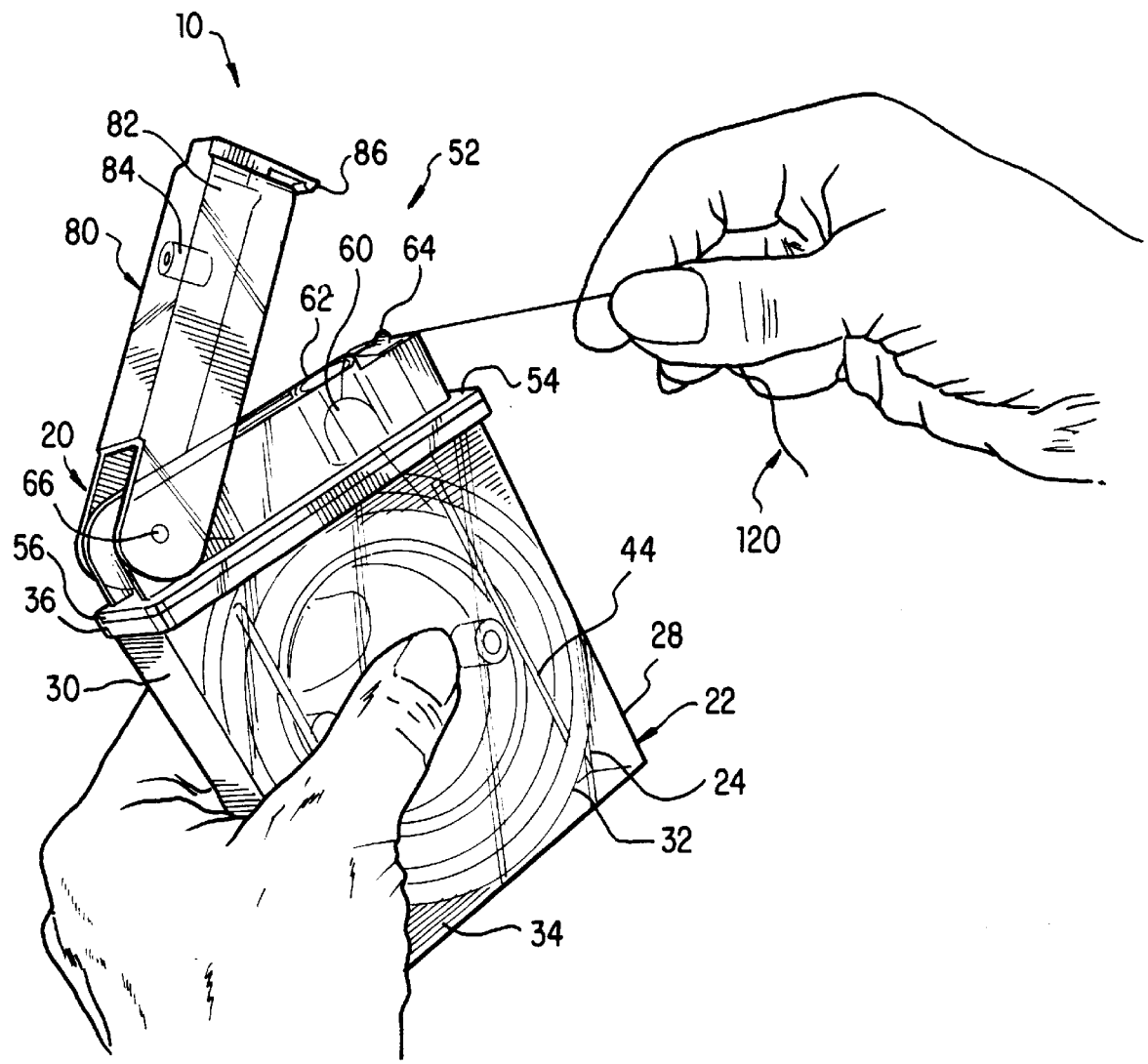
FIG. 1 is a perspective view showing a dispensing apparatus constructed according to a preferred embodiment of the present invention in operation.

FIG. 1 shows an apparatus for dispensing suture or other string material which is indicated generally by the reference numeral 10 and includes an outer casing 20 and a spool 100 disposed within casing 20. As described below, the spool 100 contains a supply of suture or other string material the end of which passes from the spool through the housing where it is grasped and cut by a user. While the invention is described herein in connection with dispensing suture, it will be recognized that any string-like or elongated material may be dispensed according to the principles of the invention.

Figure 3:
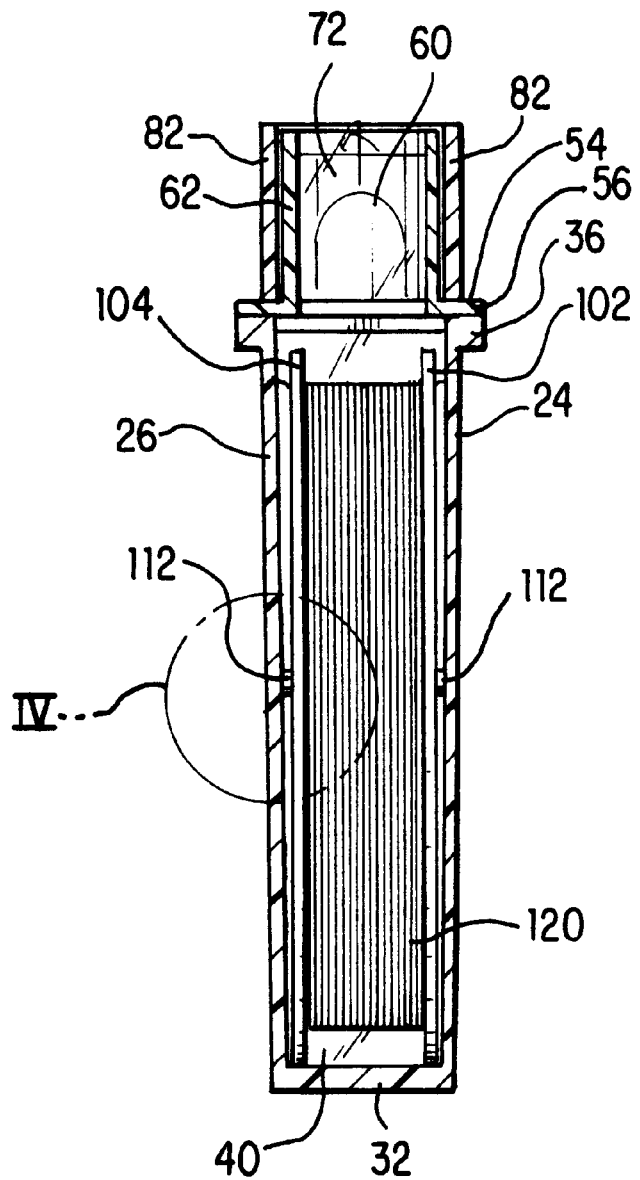
FIG. 3 is a partial sectional view of the apparatus shown in FIG. 2 taken along lines 3—3.

The outer housing or casing 20 includes a lower portion 22 and an upper portion 52 which are secured together so as to form a sealed enclosure. Lower portion 22 includes a first sidewall 24 and second sidewall 26 disclosed opposite each other and connected via endwalls 28, 30. Lower portion 22 preferably is a four-sided hollow member which is open at the top and permits spool 100 to be inserted therein, as described below. The lower end of portion 22 is closed by an arcuate bottom wall 32 which forms a hemispherical receiving portion for the spool 100. The sidewalls 24, 26 and endwalls 20, 30, however, extend past bottom panel 32 and form a hollow recessed area 34. The sidewalls 28, 30 of portion 22 may be provided with ribs 44 to provide added strength. The upper end of portion 22 comprises a flange 36 which extends around the periphery of portion 22 and outwardly past the aforementioned side and endwalls (FIG. 3). The flange 36 forms a seat to which is attached upper portion 52 of housing 20. The upper portion 52 comprises a flat base 54 and a flange portion 56 which preferably mates and aligns with flange 36 of portion 22.

After placement of spool 100 within lower portion 22, which is (or has been) filled with liquid 42, the suture or string material 120 is threaded through the upper portion 52 where it may be grasped by a user. The upper portion 52 preferably is then secured to lower portion 22 via flanges 56, 36 by any suitable means, for example, ultrasonic, thermal or chemical bonding, adhesives, or by any other fastening or bonding methods or materials. The liquid 42 may be water to keep the suture 120 moist so as to prevent it from hardening or deteriorating, or the liquid may be an antiseptic such as alcohol to maintain the suture moist and sterile.

Figure 2:
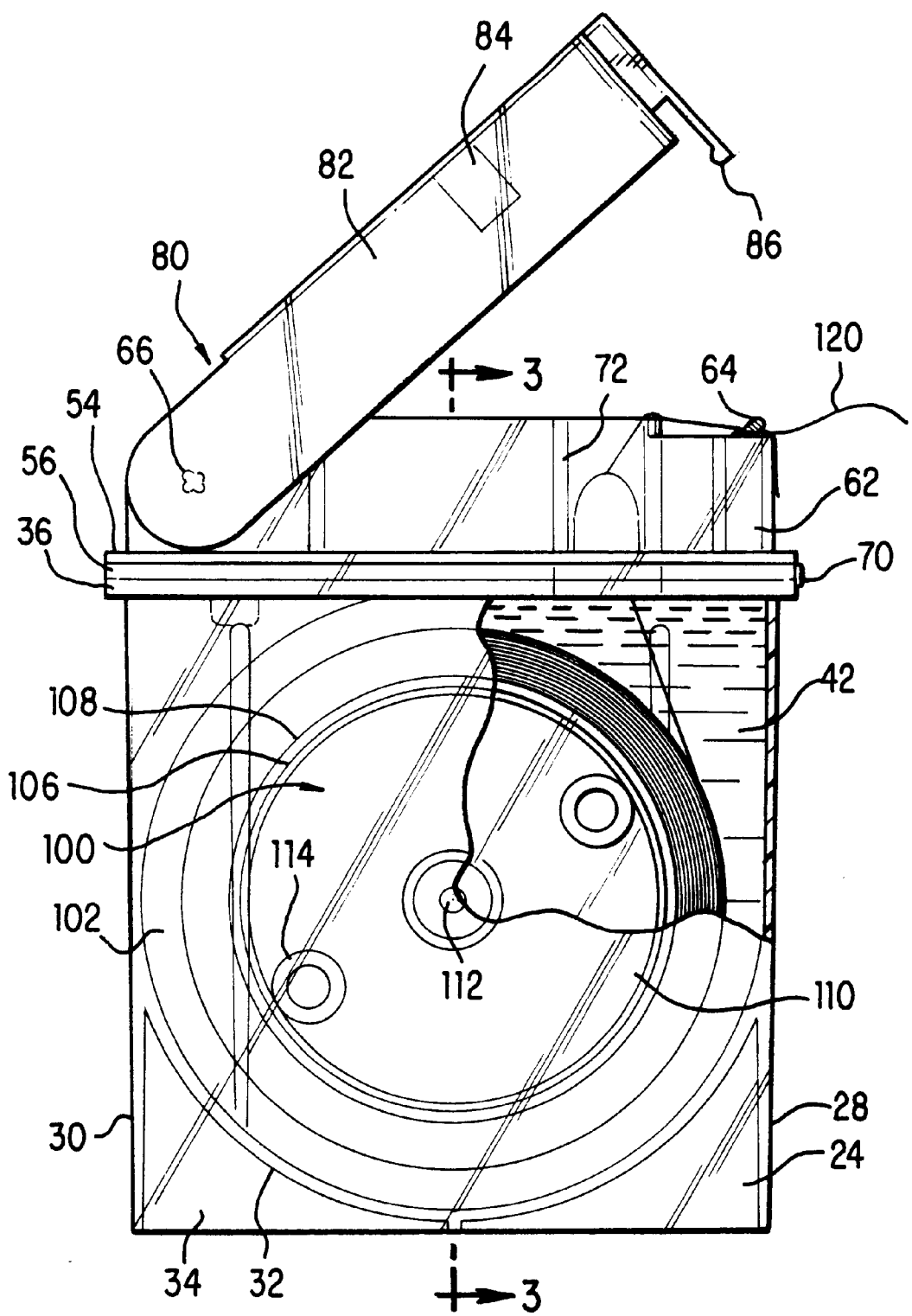
FIG. 2 is a side elevation view of the apparatus shown in FIG. 1.

The upper portion 52 of housing 20 includes upstanding plastic housing 62 which extends from base 54. A squeegee or wiper member 60 is secured to (or formed integrally with) upper portion 52. In a preferred embodiment, upstanding plastic housing 62 includes a circular boss 72 which surrounds the bullet-shaped squeegee member 60. Squeegee member 60 may have a known construction and include an elongated slit which forms an opening through which the suture 120 may be threaded. The suture 120, as seen in FIG. 2, passes from the interior of lower portion 22, through an opening formed in the flat base 54 beneath squeegee member 60, and then through squeegee member 60 where it is engaged by a cutter 64 which severs the suture 120 into desired lengths. The upper housing portion also may be provided with an anti-backlash member which contacts the spool walls and prevents the spool from continuing to rotate upon the user pulling the suture, as is known in the art.

As discussed above, the hollow interior 40 of the lower portion 22 is filled with liquid 42 in which the suture 120 is stored. In a preferred embodiment, the liquid 42 is isopropyl alcohol which maintains the suture 120 moist and in a sterile condition prior to being dispensed from device 10. The present invention provides significant benefits over prior art apparatus with respect to the use of liquid 42 to coat the suture 120. More particularly, casing 20 includes several features which provide economic benefits over prior art apparatus in that a reduced amount of antiseptic material 42 may be used. As discussed in detail below, spool 100 comprises a core with a closed periphery which results in much less liquid 42 being required to properly coat and store the suture 120. The reduction in the amount of liquid 42 which is required by each device 10 is a significant benefit that permits substantial reduction in production costs in comparison to conventional devices. The recessed bottom portion 22 of casing 20 (FIG. 2) reduces the amount of liquid 42 required to fill portion 22. The enlarged and closed core of the spool 100 of the invention, the structure of which is described below, realizes further and considerable reduction in the amount of liquid 42 required to fill the interior of casing 20.

In one embodiment, the spool 100 includes first and second circular outer walls 102, 104 (FIG. 3) joined by a center portion or core 106 which comprises a surface 108 (around which the suture 120 is wound) and a hollow interior 110. The spool has a reel-like appearance as the outer edges of outer walls 102, 104 extend past the core 106 with the suture 120 disposed therebetween. The core 106 is in the form of a hollow cylindrical tube with opposite open ends. The open ends are closed by cap members which are secured to the core. The cap members may be the outer walls 102, 104 which are secured to ends of the core 106. Optionally, the hollow core could be formed with closed ends and the outer walls 102, 104 secured thereto by any suitable means. Alternatively, the hollow core with closed ends and outer walls could be integrally formed as a unitary member. The hollow core of the spool reduces the material requirements and production costs of the apparatus and, in addition, results in a lightweight apparatus which reduces shipping costs.

Figure 4:
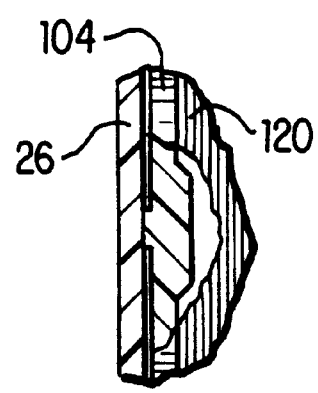
FIG. 4 is an enlarged view showing the area in circle IV of FIG. 3.

In another embodiment, the spool core is a solid member (in cross-section) and the outer walls are secured thereto (or formed integrally therewith). The core with closed ends acts as a barrier to the passage of liquid 42 and thus provides significant reduction in the amount of liquid required to fill the housing and properly coat the suture 120. Consequently, production costs are reduced as are costs associated with government regulations relating to the amount of alcohol or the like contained in such apparatus. As seen in FIGS. 3 and 4, the outer walls 102, 104 of spool 100 are provided with nibs or projections 112 which extend outwardly away from the aforesaid walls and contact the interior of sidewalls 22, 24 of the casing portion 22, for purposes explained below. A pair of bosses 114 depicted in FIG. 2 may be formed on the spool as a manufacturing expedient.

The center portion 106 of spool 100 has a substantially increased diameter relative to prior art dispensing spools in order to prevent the end portion of the suture 120 from being unusable upon removal from the device. Prior art apparatus which have a spool with a relatively small diameter core (for example, 1 inch) cause the final length of suture that is removed from the spool to be tightly curled or coiled, i.e., the end of the suture will be coiled about a diameter corresponding to the small core of the spool. This renders the final portion of the suture unusable when removed from the dispensing apparatus. However, the present invention obviates such problems in that the entire length of suture 120 wound about surface 108 of spool core 106 is usable when removed from the spool 100 and device 10. When the final length of suture 120 is removed from the spool 100, due to the size and configuration of the spool, it is not tightly coiled or otherwise distorted from its usual string-like orientation or configuration. Preferably, the diameter of the center core of the spool is greater than approximately 2 inches. In a preferred embodiment, the diameter of the central portion 106 of spool 100 is approximately 2.5 inches. A person skilled the art, of course, will appreciate that the size of the spool core may be further varied while still providing a base which permits the entire length of suture to be usable.

The upper portion 52 of casing 20 comprises a cap 80 which is hingedly attached thereto. The cap 80 comprises elongated sidewalls 82, the rearward ends of which are pinned at 66 to the upstanding portion 62 of upper housing portion 52. The pivot connection 66 permits the cap 80 to be moved toward and away from housing 20. The suture 120 which is removed from spool 100 and passes through squeegee member 60 is pulled to a desired length by a user and cut on element 64. After the suture has been cut, a length of suture remains in cutter 64 and extends from the cutter to the squeegee member 60. In order to prevent antiseptic material 42 from leaking out of casing 20 via squeegee member 60, cap 80 is provided with a projection 84 which enters circular boss 72 of upper housing portion 52 and contacts squeegee member 60 so as to occlude the opening therein. Subsequent movement of the housing with the cap closed thus does not result in any fluid escaping. The cap 80 is provided with a locking lip 86 which is configured to engage a locking projection 70 formed on one end of the flange 56 of upper portion 52 of housing 20 (FIG. 2), the projection 70 and locking lip 86 cooperating to close the cap when the device 10 is not in use.

A significant aspect of the present invention permits the suture 120 to be removed via the rotation of spool 100 while a user grasps the sidewalls of the container in one hand. As seen in FIG. 1, a user may grasp sidewalls 24, 26 of housing portion 22 in one hand, necessarily applying force thereto to properly grasp the device, and may withdraw the suture 120 using the other hand. As discussed above, operating prior art apparatus in such a manner caused significant problems due to the spool being braked by the user's one hand. That is, squeezing the sidewalls of the housing portion adjacent the spool caused the housing sidewalls to flex into the spool walls, thereby slowing or stopping the rotation of the spool and preventing proper dispensing of the suture. As such, the user of a prior art apparatus often would hold the device in one hand, as shown in FIG. 1, and would remove the suture with the other hand until the point at which the suture would no longer move freely (due to the force being applied against the spool by the user's one hand). This often resulted in the suture breaking.

The apparatus 10 constructed according to the present invention, however, overcomes such problems and permits smooth and free rotation of the spool 100 within casing portion 22 despite the user grasping or squeezing the housing walls (as seen in FIG. 1). To prevent such handling of the housing from slowing or stopping rotation of the spool, the outer spool walls 102, 104 are provided with nibs or projections 112. The projections 112 extend from the spool and contact the interior of casing walls 24, 26, as best seen in FIG. 4. As a result, a user can grasp sidewalls 24, 26, for example between the thumb and forefinger, and apply considerable pressure so as to securely hold the device 10, and also grasp and pull the end of suture 120 so as to rotate the spool until the desired amount of suture has been removed. The projections 112 provide a slight gap between the walls 102, 104 of spool 100 and the walls 24, 26 of housing portion 22 such that slight flexing by a user does not result in the housing walls contacting and braking the spool walls 102, 104.

The projections 112 preferably are located along the central axis of the circular walls 102, 104 of spool 100 (and at the center of the sidewalls 24, 26 of housing portion 22). In use, the user typically grasps the device such that the thumb and forefinger are located near the center of the sidewalls of the housing and the spool. By positioning the projections 112 in this area, the applied force causes the projections to abut the center of the spool walls 102, 104 in an axle-like manner which does not significantly affect the rotation of spool 100. The present inventors conducted tests in order to verify the improvement provided by the present invention with respect to the amount of force that may be applied against the sidewalls of the housing without adversely affecting withdrawal of the suture from the device. Various forces were applied to the sides of the housing while the force required to withdraw the suture was measured. The results of the tests are set forth below.

|  | Force applied to housing | Force required to withdraw suture (lbs.) | |
|---|---|---|---|
| Prior art dispenser | 0 | 0.1 | |
|  | 15 | 0.1 | |
|  | 20 | 1 | |
|  | 25 | 2 | |
|  | 30 | 4 | |
|  | 32 | 5 suture broke | |
|  |  | (Dry) | (Alcohol) |
| Invention | 0 | 0.2 | 0.1 to 0.4 |
|  | 32 | 0.5 to 2 on jerks | 0.3 to 0.6 |
|  | 40 | 1 to 2 on jerks | 0.2 to 0.4 |
|  | 50 | 1 to 2.5 on jerks | 0.4 to 1.5 |
|  | 60 | 1 to 2.5 on jerks | 0.8 to 2 |
|  | 60 | (offcenter-locks up) | 1 to 2.5 |
|  | 68 | (n/a) | 1 to 2 |
|  | 68 | (offcenter n/a) | 1 to 2.5 |

The above test results indicate that the suture dispensing device constructed according to a preferred embodiment of the invention provides great improvement over prior art devices. For example, when a force of 32 lbs./inch$^2$ was applied to the housing of the prior art dispenser device, a force of 5 lbs. was required to withdraw the suture (which broke). However, when a force of 32 lbs./inch$^2$ was applied against the suture dispenser of the present invention, only a force in the range of 0.5 to 2 lbs was required to withdraw the suture. Further, when the dispenser of the invention included isopropyl alcohol, only 0.6 pounds of force was required to withdraw the suture despite the 32 lbs./inch$^2$ force which was applied against the cassette housing. As such, squeezing the sides of a dispensing device constructed according to the present invention has very little effect on the ability to withdraw the suture. This feature of the present invention provides a significant benefit over prior art devices and overcomes the above-described problems relating to suture withdrawal. Those skilled in the art, of course, will appreciate that the device depicted in the Figures and discussed above is but an exemplary application of the principles of the present invention. For example, the projections 112 could be applied off-center relative the spool walls 102, 104 and/or the casing walls 24, 26. Further, the projections 112, rather than being formed on the walls 102, 104 of the spool 100, could be formed on the walls 24, 26 of casing 20. Further still, a projection could be formed on an outer wall of the spool at one side of the apparatus, and another projection could be formed on the side wall of the housing at the opposite side of the apparatus. Also, a plurality of projections could be utilized on one or both walls of either the spool or housing. In yet another embodiment, the projections may be comprised by the ends of an axle disposed in the hollow core of the spool, the axle ends contacting the housing walls upon the application of force to same. Other variations are possible as will be recognized by those skilled in the art.

It is apparent that the present invention provides greatly improved operation and considerable benefits relative to prior art devices for dispensing suture. The invention overcomes the problem with prior art devices in which the terminal portion of a supply of suture wound on the spool is rendered unusable when removed from the spool because it is tightly coiled and difficult to handle. The spool of the invention obviates such problem and renders the entire supply of suture stored thereon usable in an uncoiled fashion. Another aspect of the present invention greatly reduces the amount of liquid, for example antiseptic material such as isopropyl alcohol, which is required to fill the container in which the suture is stored. The spool has a closed core which prevents the passage of fluid or other material thereby. Thus, the fluid is only required to be present between the outer surface of the spool and the walls of the container. This provides considerable cost savings compared with prior art devices which typically utilized spools the interiors of which were filled with alcohol. Also, the core of the spool which is provided with a closed exterior is preferably hollow so as to reduce material requirements and lower both manufacturing and shipping costs.

Finally, the present invention overcomes problems associated with prior art apparatus regarding handling of the device while dispensing the suture. The present invention permits a user to grasp and apply force to the sides of the housing while withdrawing the suture because the housing walls do not slow or stop rotation of the spool. This feature also provides significant benefits over prior art suture dispensing apparatus which did not permit such handling.

While the above invention has been described in connection with dispensing suture material which has been stored or soaked in liquid such as alcohol, persons skilled in the art will appreciate that the principles of the invention are equally applicable to the dispensing of various string-like or other elongated materials from a housing utilizing a spool which may be stored in liquid (or any other fluent or solid material). The description of preferred embodiments made above is but for the sake of completeness and clarity and should in no way be construed as limiting the present invention to a fluid filled cassette for dispensing suture.

Accordingly, it will be apparent to those skilled in the art that various changes and modifications may be made to the embodiments illustrated herein without departing from the spirit of the invention or scope of the appended claims.

What is claimed is:

1. Hand-held apparatus for dispensing a supply of string material having an end portion comprising a housing for providing a sealed enclosure which is structured and arranged to contain a liquid for contacting the string material, said housing including first and second opposite semi-flexible housing side walls, each of said first and second semi-flexible housing side walls including an inner surface, a spool positioned within said housing and freely rotatable within said housing, said spool including first and second spool side walls and an inner core, whereby said supply of string material can be wrapped around said inner core with said end portion of said supply of string material extending from said housing for dispensing said string material by pulling on said end portion while grasping said first and second housing side walls to rotate said spool and dispense said string material from said housing, and at least one separation member disposed between said inner surface of one of said first and second housing side walls and said corresponding one of said first and second spool side walls maintaining a gap between said inner surface of said one of said first and second housing side walls and said corresponding side of said first and second spool side walls except for said at least one separation member, wherein said housing including an inner arcuate bottom wall extending from the inner surface of one of the first and second housing side walls to the inner surface of the other of the first and second housing side walls for directly supporting both the first and second spool side walls, whereby when said first and second housing side walls are grasped thereby flexing said semi-flexible side walls said one of said first and second housing side walls is prevented from contacting said corresponding one of said first and second spool side walls and retarding the rotation of said spool therein.

2. The hand-held apparatus of claim 1 including a pair of said separation members disposed between said inner surfaces of both of said first and second housing side walls and said corresponding first and second spool side walls, whereby a gap is maintained between both said first and second housing side walls and said first and second spool side walls.

3. The hand-held apparatus of claim 2 wherein said pair of separation members are located at the central axis of said spool.

4. The hand-held apparatus of claim 1 wherein said at least one separation member is permanently affixed to and projects from said one of said first and second spool side walls.

5. The hand-held apparatus of claim 1 wherein said supply of string material comprises a supply of suture material.

6. The hand-held apparatus of claim 5 wherein said sealed enclosure is at least partially filled with said liquid for contacting said supply of suture material therein.

7. The hand-held apparatus of claim 6 wherein said inner core is substantially free of any liquid.

8. The hand-held apparatus of claim 7 wherein said inner core is substantially hollow.

9. The hand-held apparatus of claim 7 wherein said inner core is substantially solid.

10. The hand-held apparatus of claim 6 wherein said liquid comprises an antiseptic liquid.

11. The hand-held apparatus of claim 6 including a wiper member for removing excess liquid from said suture material being withdrawn from said housing, said wiper member including an opening through which said suture material passes.

12. The hand-held apparatus of claim 1 including an axle passing through said inner core of said spool, said at least one separation member comprising at least one end of said axle.

13. The hand-held apparatus of claim 1 wherein the outside diameter of said inner core is 2.5 inches.

14. The hand-held apparatus of claim 1 wherein said string material comprises suture material and said liquid comprises an antiseptic liquid.

* * * * *

UNITED STATES PATENT AND TRADEMARK OFFICE
CERTIFICATE OF CORRECTION

PATENT NO. : 5,911,829
DATED : June 15, 1999
INVENTOR(S) : Maksudian et al.

It is certified that error appears in the above-indentified patent and that said Letters Patent is hereby corrected as shown below:

Column 6, line 3, after "to housing" insert --(psi)--.

Signed and Sealed this

Ninth Day of November, 1999

Attest:

Q. TODD DICKINSON

*Attesting Officer*    *Acting Commissioner of Patents and Trademarks*